(12) United States Patent
Liu et al.

(10) Patent No.: US 6,387,545 B1
(45) Date of Patent: May 14, 2002

(54) ORGANIC HOLE TRANSPORTING AND BLUE LIGHT EMITTING ELECTROLUMINESCENT MATERIALS

(75) Inventors: Jia-Ming Liu; Huan-Lurn Hsieh; Po-Yen Lu; Ying-Chuan Wang, all of Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/292,773

(22) Filed: Apr. 14, 1999

(51) Int. Cl.$^7$ .................. H05B 33/12; C07C 211/54
(52) U.S. Cl. .................. 428/690; 428/704; 428/917; 313/504; 313/506; 564/307; 564/395; 564/405
(58) Field of Search ................. 428/690, 704, 428/917; 313/504, 506; 564/307, 395, 405, 433

(56) References Cited

U.S. PATENT DOCUMENTS

| | | | | |
|---|---|---|---|---|
| 5,126,214 A | * | 6/1992 | Tokailin et al. | 428/690 |
| 5,150,006 A | * | 9/1992 | Van Slyke et al. | 313/504 |
| 5,503,910 A | * | 4/1996 | Matsuura et al. | 428/212 |

\* cited by examiner

Primary Examiner—Marie Yamnitzky

(74) Attorney, Agent, or Firm—W. Wayne Liauh

(57) ABSTRACT

A tertiary amine imparted quaterphenyl compound represented by the following formula:

(Formula I)

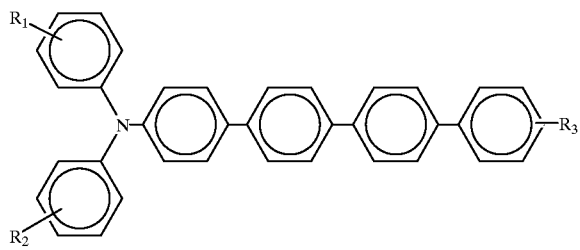

where $R_1$ and $R_2$, which can be different or the same, are hydrogen, $C_1$–$C_5$ alkyl, or $C_6$–$C_{12}$ aryl, and $R_3$ is hydrogen, $C_1$–$C_5$ alkyl, a vinyl group, or an aryl vinyl group. The tertiary amine-imparted quaterphenyl compound exhibits good blue light luminescence and hole-transportability, and can be used in forming a hole-transporting layer, a blue light emitting layer, or a combined hole-transporting and light emitting layer of a light emitting organic electroluminescent device. Examples of the quaterphenyl compounds include N-quaterphenyl-4-yl-N,N-diphenylamine, N-(4'-(1,1-diphenylvinyl)quaterphenyl-4-yl)-N-phenyl-N-(m-tolyl)amine, or N-quaterphenyl-4-yl-N-phenyl-N-(m-tolyl)amine.

20 Claims, 3 Drawing Sheets

ORGANIC HOLE TRANSPORTING AND BLUE LIGHT EMITTING ELECTROLUMINESCENT MATERIALS

FIELD OF THE INVENTION

The present invention relates to a novel organic electroluminescent material and the improved organic electroluminescent devices prepared therefrom. More specifically, the present invention relates to a novel family of organic compounds for use in organic electroluminescent devices which not only provide enhanced electroluminescence in the blue color range so that they can be advantageously used as the light emitting layer of the organic electroluminescent device, but which also provide a hole injection capability so that they can also be used as the hole injection layer. By merging the blue light emitting layer with the hole injection layer, the present invention allows the blue light emitting organic electroluminescent devices to be simplified, while, at the same time, it also improves the blue emitting efficiency of the organic electroluminescent devices so constructed.

BACKGROUND OF THE INVENTION

Organic electroluminescent devices are becoming an increasingly important category of thin film organic semiconductor devices. An organic electroluminescent device operates by applying an external electric field, wherein electrons enter from the cathode and holes enter from the anode, of the organic electroluminescent device. When the electrons and the holes meet after they travel through the electron transport layer and the hole transport layer, respectively, energy will be generated in the form of light (luminescence). This is a short-hand description of the organic electroluminescent phenomenon. Organic electroluminescent devices provide the advantages of self-luminescence, wide viewing angle, high response rate, simple fabrication, and low power consumption, and are thus excellent candidates for use in flat panel displays.

Typically, the organic electroluminescent devices have a multi-layered structure, comprising an hole injection layer, a light emitting layer, and an electron injection layer. The hole injection layer and electron injection layer also provide the functions to transport holes and electrons, respectively. This is illustrated in U. S. Pat. No. 5,151,629.

U.S. Pat. No. 4,539,507 discloses an electroluminescent device which comprises, in sequence, an anode electrode, a hole-injecting zone, an organic luminescent zone, and a cathode electrode, at least one of the electrodes being capable of transmitting at least 80% of radiation having wavelengths longer than 400 nm. The organic luminescent zone comprises an electron-transporting compound that provides a maximum electroluminescent quantum efficiency of at least about $5 \times 10^{-4}$ photons/electron. The hole-injecting zone consists essentially of 1,1-bis-(4dipolylaminophenyl)-cyclohexane, and the hole-injecting zone and the luminescent zone having a combined thickness of no more than 1 micron. The cathode is an indium cathode. Typically, as taught in the '629 patent, a separate luminescent layer is provided separately from the electron-transporting layer, in order to allow maximum choice for each individual layer and achieve best luminescence efficiency.

Another important requirement in the development of organic electroluminescent devices is to develop RGB (red, green, and blue) light emitting devices so as to satisfy the need of a color flat panel display. At the present time, green organic electroluminescent devices have seen the most successful development. Examples of prior art references that teach green organic electroluminescent devices include U.S. Pat. Nos. 4,769,292 and 5,227,252. In both references, green organic electroluminescent devices with a half-time life of more than 10,000 hours and a luminescence of 1,000 cd/m². Red organic electroluminescent devices are discussed in U.S. Pat. Nos. 5,409,783 and 5,432,014. However, at the present time, the wavelength of luminescence emitted by these devices do not satisfy the CIE standard specified for red light.

U.S. Pat. Nos. 5,077,142 and 5,389,444 taught blue organic electroluminescent devices. However, the luminescence of blue light from these devices are only about 100 cd/m². At such a low luminescence, these devices have very limited practical use.

Because of the increasing popularity and thus importance of flat panel displays, it is highly desirable to develop new organic compounds that can be advantageously used in the low power consumption organic electroluminescent devices which can emit luminescence especially in the red and blue color spectra. At the present time, there is a lack of good organic electroluminescence compounds that will satisfy this need.

SUMMARY OF THE INVENTION

The primary object of the present invention is to develop an improved organic electroluminescent device in the blue color range. More specifically, the primary object of the present invention is to develop an improved organic compound which can provide improved luminescence in the blue color range, as well as simplify the construction of organic electroluminescent devices.

In the present invention, it was discovered by the co-inventors that, by incorporating a tertiary amine group into a organic blue luminescence compound, the tertiary amine imparts a hole-transportability and hole-injectivity into the organic blue luminescence compound. One of the main advantages of the discovery made in the present invention is that the addition of the tertiary amine group to the organic blue luminescence compound does not adversely affect its blue luminescence; it actually enhances it. Thus, the tertiary amine imparted organic blue luminescence compound can be used as a combined light emitting/hole transporting layer to greatly simply the construction of an organic electroluminescent device. The elimination of the hole transport layer can also reduce power consumption and improve the luminescence of the organic electroluminescent device.

In a preferred embodiment of the present invention, the tertiary amine group is imparted into a quaterphenyl compound to form the following compound:

(Formula I)

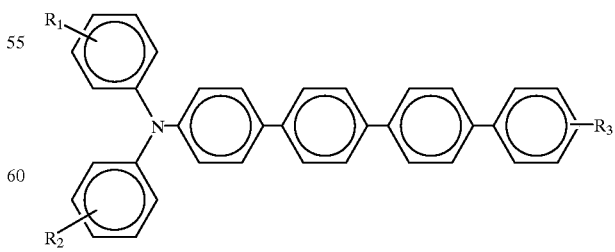

where $R_1$ and $R_2$, which can be different or the same, are hydrogen, $C_1$–$C_5$ alkyl, or $C_6$–$C_{12}$ aryl, and $R_3$ is hydrogen, $C_1$–$C_5$ alkyl, a vinyl group, or an aryl vinyl group.

The tertiary amine group imparted quater phenyl compound shown above can be synthesized according to either of the following methods.

Method 1:

In this method, the quaterphenyl compound is first iodized and the iodized quaterphenyl compound is then reacted with a secondary amine in a catalyzed reaction as follows:

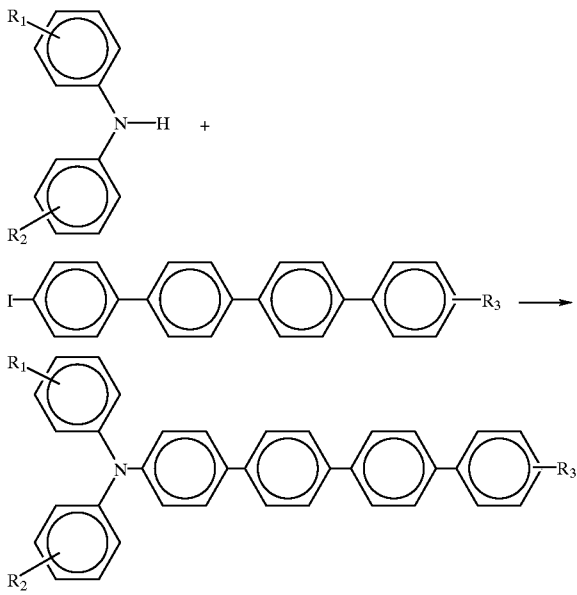

Method 2:

In the second method, a tertiary amine-substituted tertiaryphenyl compound is reacted with an aryl Grignard reagent in the presence of a catalyst to form a tertiary-substituted quaterphenyl compound. The second method is summarized in the following reaction:

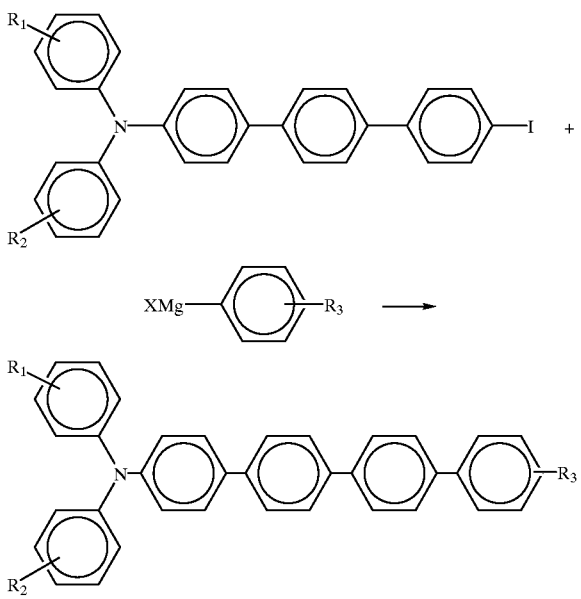

where X is Cl, Br, or I.

The organic blue luminescence compound of the present invention can be used in a two-layer or a three-layer configuration. Both configurations include an electron-transport layer. In the two-layer configuration, the organic blue luminescence compound doubles both as a blue luminescence layer and as a hole transport layer. In the three-layer configuration, an additional hole-transport layer is included.

Preferably, the electron-transport material in the electron-transport layer is a metal chelate, such as aluminum tris(8-hydroxyquinoline), bis(10-hydroxybenzo[h]quinolinato) beryllium; 1,3,4-oxadiazole or 1,2,4-triazole derivative or its derivative; a thiopyran sulfone or its derivative; or bis (benzimidazolyl)berylenedicarboximide; etc.

If a separate hole-transport layer is to be used in addition to the dual-function tertiary amine imparted quaterphenyl compound disclosed in the present invention, preferably, the hole-transport material in the hole-transport layer is a triarylamine, such as N,N'-diphenyl-N,N'-bis(3-methylphenyl)-4,4'-diamine, N,N,N'N'-tetrakis-(4-methylphenyl)-(1,1'-biphenyl)-4,4'-diamine, N,N'-bis-(1-naphthyl)-N,N'-diphenyl-1,1'-biphenyl-4,4"-diamine, or 4,4',4"-tris(3-methylphenylpnehylamino)triphenylamine, etc. On the other hand, the tertiary amine imparted quaterphenyl compound can also be used as a hole-transport material in a multi-layered organic electroluminescent device which uses other light emitting materials.

In preparing the organic electroluminescent devices, all the organic layers can be deposited by sputtering under a vacuum. Preferably, the electron-transport layer has a thickness of 50 Å to 1,500 Å, more preferably 300 Å to 700 Å. The hole-transport layerpreferablyhas a thickness of200 Å to 1,000 Å, more preferably 300 Å to 600 Å. The light emitting layer preferably has a thickness of 100 Å to 1,500 Å, more preferably 200 Å to 700 Å. If the tertiary amine imparted quaterphenyl compound is used as both the hole-transport layer and the light emitting layer, its preferred thickness can fall into either range. The anode material can be a high work function metal oxide, such as indium tin oxide, tin oxide, indium oxide, or zinc oxide. And the cathode material can be a low function metal, such as lithium, magnesium, calcium, beryllium, potassium, strontium, Mg:Ag alloy, or Li:Al allry. The cathode material can also be a metal compound, such as lithium fluoride, calcium oxide, strontium oxide, etc.

BRIEF DESCRIPTION OF THE DRAWING

The present invention will be described in detail with reference to the drawing showing the preferred embodiment of the present invention, wherein.

DETAILED DESCRIPTION OF THE PREFERRED EMBODIMENT

Figure 1:
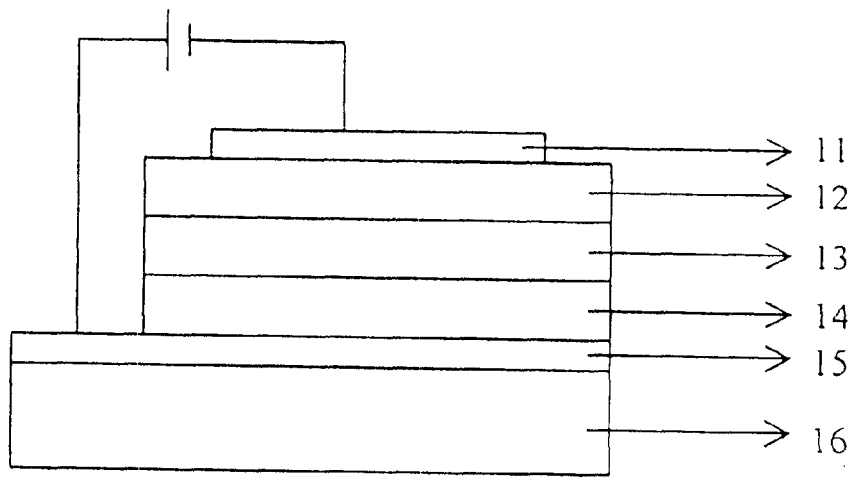
FIG. 1 is a schematic side view showing a prior art three-layered organic electroluminescent device.

The present invention discloses an improved organic electroluminescent device in the blue color range utilizing a novel tertiary amine imparted quaterphenyl compound which can be used in preparing the light emitting layer, which also doubles as the hole transmission layer, so as to provide improved luminescence in the blue color range, as well as simplify the construction of organic electroluminescent devices. It was discovered in the present invention that the incorporation of a tertiary amine group into an organic blue luminescence compound imparts a hole-transportability and hole-injectivity into the organic blue luminescence compound. Such a discovery provides a very useful practical application in that the addition of the tertiary amine group onto the organic blue luminescence compound does not adversely affect its blue luminescence; in fact, it enhances the blue luminescence. Thus, the tertiary amine imparted organic blue luminescence compound can be used as a combined light emitting/hole transporting layer to greatly simply the construction of an organic electroluminescent device. The elimination of the hole transport layer reduces power consumption and improves the luminescence of the organic electroluminescent device.

In a preferred embodiment of the present invention, the original blue organic electroluminescent compound is a quaterphenyl compound and the tertiary amine group is imparted into a quaterphenyl compound to form the following compound:

(Formula I)

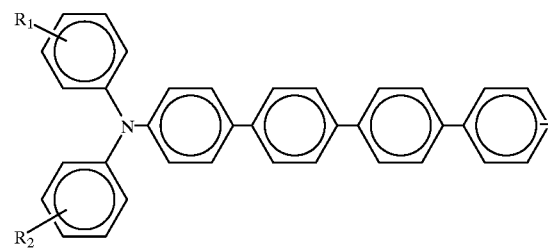

where $R_1$ and $R_2$, which can be different or the same, are hydrogen, $C_1$–$C_5$ alkyl, or $C_6$–$C_{12}$ aryl, and $R_3$ is hydrogen, $C_1C_5$ alkyl, a vinyl group, or an aryl vinyl group.

The tertiary amine group imparted quater phenyl compound shown above can be synthesized according to either of the following methods.

Method 1:

In this method, the quaterphenyl compound is first iodizied and the iodized quaterphenyl compound is then reacted with a secondary amine in a catalyzed reaction as follows:

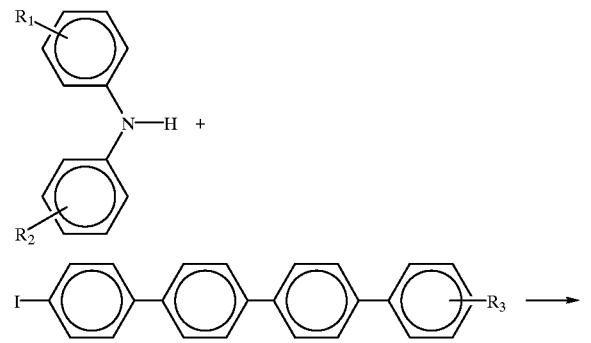

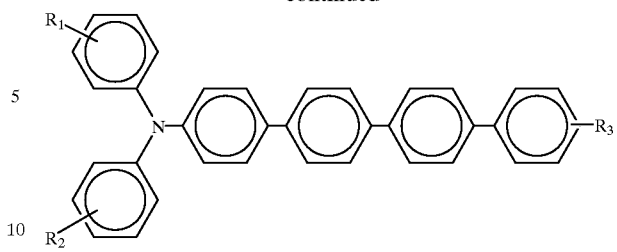

Method 2:

In the second method, a tertiary amine-substituted tertiaryphenyl compound is reacted with an aryl Grignard reagent in the presence of a catalyst to form a tertiary amine-substituted quaterphenyl compound. The second method is summarized in the following reaction:

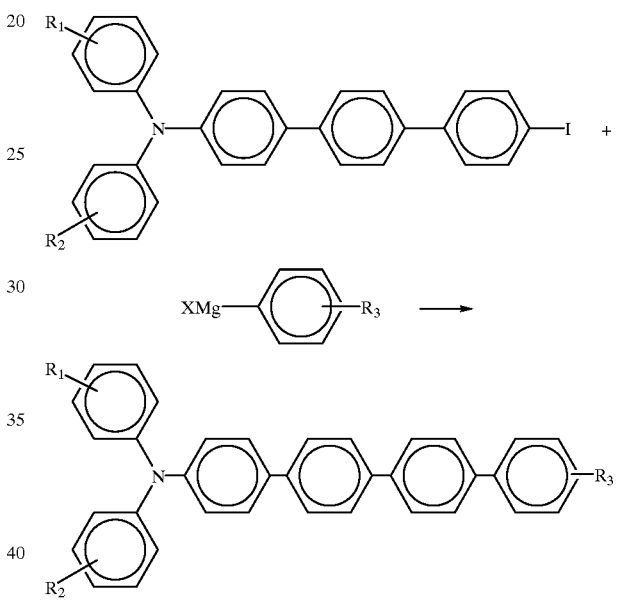

where X is Cl, Br, or I.

The organic blue luminescence compound of the present invention can be used in a two-layer or a three-layer configuration. Both configurations include an electron-transport layer. In the two-layer configuration, the organic blue luminescence compound doubles as both a blue luminescence layer and a hole transport layer. In the three-layer configuration, an additional hole-transport layer is included.

Preferably, the electron-transport material in the electron-transport layer is a metal chelate, such as aluminum tris(8-hydroxyquinoline) or bis(10-hydroxybenzo[h]quinolinato) beryllium; 1,3,4-oxadiazole or 1,2,4-triazole or its derivative; a thiopyran sulfone or its derivative; or bis(benzimidazolyl)perylenedicarboximide; etc.

If a separate hole-transport layer is to be used in addition to the dual-function tertiary amine imparted quaterphenyl compound disclosed in the present invention, preferably, the hole-transport material in the hole-transport layer is a triarylamine, such as N,N'-diphenyl-N,N'-bis(3-methylphenyl)-4,4'-diamine, N,N,N'N'-tetrakis-(4-methylphenyl)-(1,1'-biphenyl)-4,4'-diamine, N,N'-bis-(1-naphthyl)-N,N'-diphenyl- 1,1'-biphenyl-4,4"-diamine, or 4,4',4"-tris(3-methyl-phenylpnehylamino)triphenylamine, etc. On the other hand, the tertiary amine imparted quaterphenyl compound can also be used as a hole-transport material in a multi-layered organic electroluminescent device which uses other light emitting materials.

In preparing the organic electroluminescent devices, all the organic layers are deposited by sputtering under a vacuum. Preferably, the electron-transport layer has a thickness of 50 Å to 1,500 Å, more preferably 300 Å to 700 Å. The hole-transport layer preferably has a thickness of 200 Å to 1,000 Å, more preferably 300 Å to 600 Å. The light emitting layer preferably has a thickness of 100 Å to 1,500 Å, more preferably 200 Å to 700 Å. If the tertiary amine imparted quaterphenyl compound is used as both the hole-transport layer and the light emitting layer, its preferred thickness can fall into either range. The anode material can be a high work function metal oxide, such as indium tin oxide, tin oxide, indium oxide, or zinc oxide. And the cathode material can be a low function metal, such as lithium, magnesium, calcium, beryllium, potassium, strontium, Mg:Ag alloy, or Li:Al allry. The cathode material can also be a metal compound, such as lithium fluoride, calcium oxide, strontium oxide, etc.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

Synthesis of 4-Iodoquaterphenyl

To a first mixture containing 5.0 g of quaterphenyl, 8.28 g of iodine, 75 ml of glacial acetic acid, 10 ml of carbon tetrachloride and 2.51 g of urea, a second mixture containing 7.5 ml of concentrated sulfuric acid and 2.00 ml of nitric acid (d=1.4) was added over a period of 0.5 hours while the first mixture was stirred at 115–117° C. Heating continued for another 2.5 hours. The product then was cooled, filtered, washed with sodium bisulphite ($NaHSO_3$), water and methylene chloride. The reaction yield was 35%.

EXAMPLE 2

Synthesis of N-quaterphenyl-4-yl-N,N-diphenylamine

A mixture containing 2.05 g of diphenylamine, 5.00 g of 4-iodoquaterphenyl prepared in Example 1,6.74 g of powdered anhydrous potassium carbonate, 1.54 g of electrolytic copper powder and 0.32 g of 18-crown-6-ether was prepared and refluxed in 30 ml sulpholane under nitrogen for six hours. The mixture was extracted with water and methylene chloride, and the acquisition was removed. The organic layer was dried with magnesium sulphate, followed by the removal of copper and the inorganic salts by filtration. The solvent was distilled under reduced pressure. The residue then was freed from diphenylamine by ether, and from the crown ether and most impurities by passing it through a silica gel column. The final diphenyl quaterphenylamine product was then isolated by recrystalization. The yield was 91%.

EXAMPLE 3

Synthesis of N-guaterphenyl-4-yl-N-phenyl-N-(m-tolyl)amine

A mixture containing 0.5 1 g of 3-methyl diphenylamine (only one of the phenyl groups is attached with a methyl group), 1.03 g of 4-iodoquaterphenyl prepared in Example 1, 1.49 g of powdered anhydrous potassium carbonate, 0.36 g of electrolytic copper powder and 0.08 g of 18-crown-6-ether was prepared and refluxed in 10 ml sulpholane under nitrogen for six hours. The mixture was extracted with water and methylene chloride, and the acquisition was removed. The organic layer was dried with magnesium sulphate, followed by the removal of copper and the inorganic salts by filtration. The solvent was distilled under reduced pressure. The residue was freed from the 3-methyl diphenylamine by ether, and from the crown ether and most impurities by passing it through a silica gel column. The final product of 3-methyl diphenyl quaterphenylamine was then isolated by recrystalization. The yield was 89%.

EXAMPLE 4

Synthesis of N-(4'-(1,1-diphenylvinyl)quaterphenyl-4-yl)-N-phenyl-N-(m-tolyl)amine A mixture containing 2.8 g of a Grignard reagent of2-(4-chloro-phenyl)-1,1-diphenyl ethene, 5 g of 3-methyl dipnehyl-4-iodo-p-terphenylamine and 0.048 g of nickel chloride (dppp) was prepared and stirred in a liquid mixture containing 20 ml of tetrahydrofuran (THF) and 20 ml of toluene under nitrogen for six hours. The mixture was quenched by methanol. The solvent was removed under reduced pressure and the final produced was isolated by chromatography. The yield was 75%.

EXAMPLE 5

Preparation of a Two-layered Organic Electroluminescent Device

Figure 2:
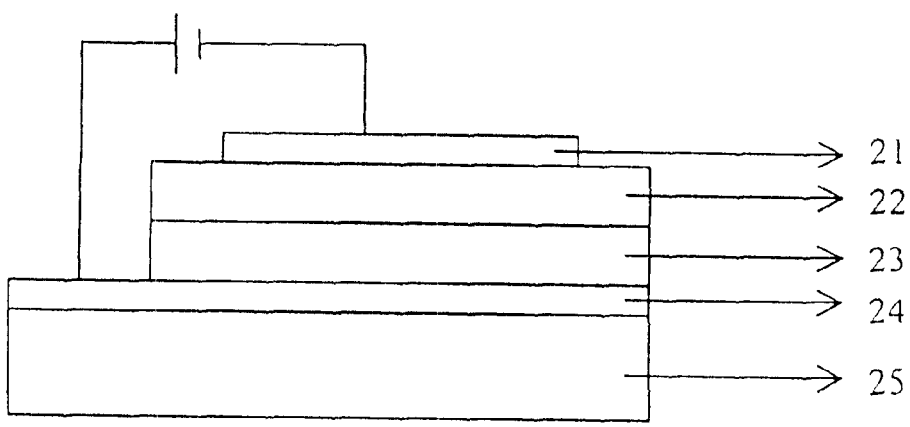
FIG. 2 is a schematic side view showing a two-layered organic electroluminescent device of the present invention wherein the hole-transport layer is merged with the light emitting layer.
Figure 3:
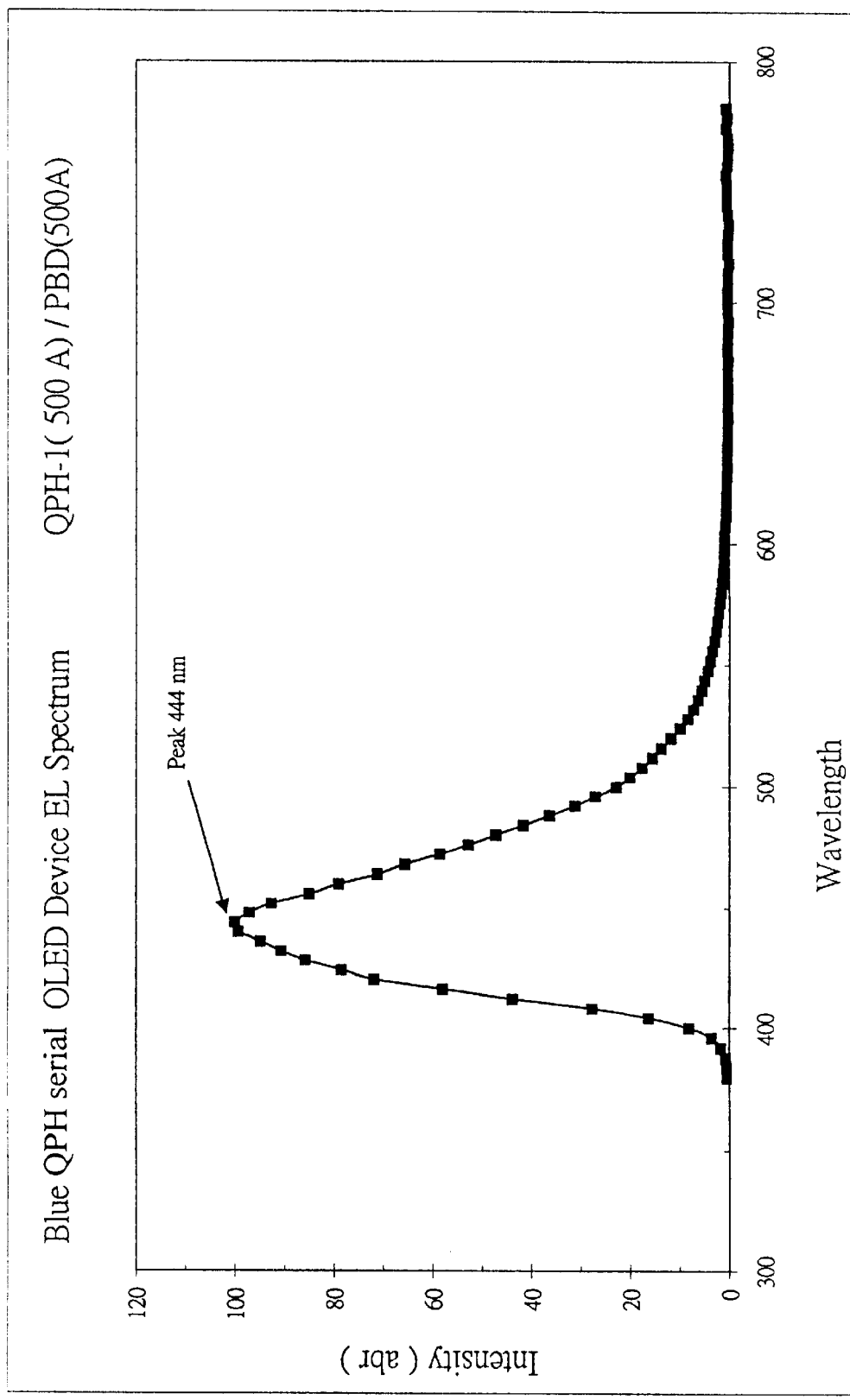
FIG. 3 is a light spectrum from a two-layered organic electroluminescent device incorporating the tertiary amine imparted quaterphenyl compound of the present invention.

FIG. 2 is a schematic side view showing a two-layered organic electroluminescent device of the present invention wherein the hole-transport layer is merged with the light emitting layer. On a clean ITO glass 24 formed on a substrate 25, a tertiary amine imparted quaterphenyl compound (QPH) prepared from one of the above examples was deposited under vacuum ($5\times10^{-6}$ Torr) to a depth of 500 Å. This serves as a combined hole-transporting and light emitting layer 23. Then biphenyl-p-(t-butyl)phenyl-1,3,4-oxadiazole (PBD) was deposited on the QPH layer to a depth of 500 Å to serve as an electron-transporting layer 22. Finally a Mg:Ag=10:1 alloy was deposited to serve as a cathode 21. The ITO glass 24 also serves as an anode. This completed the construction of the two-layered organic electroluminescent device. An electric current of 20 mA was applied to emit a blue color light. The light spectrum is shown in FIG. 3.

EXAMPLE 6

Preparation of a Three-layered Organic Electroluminescent Device

Figure 4:
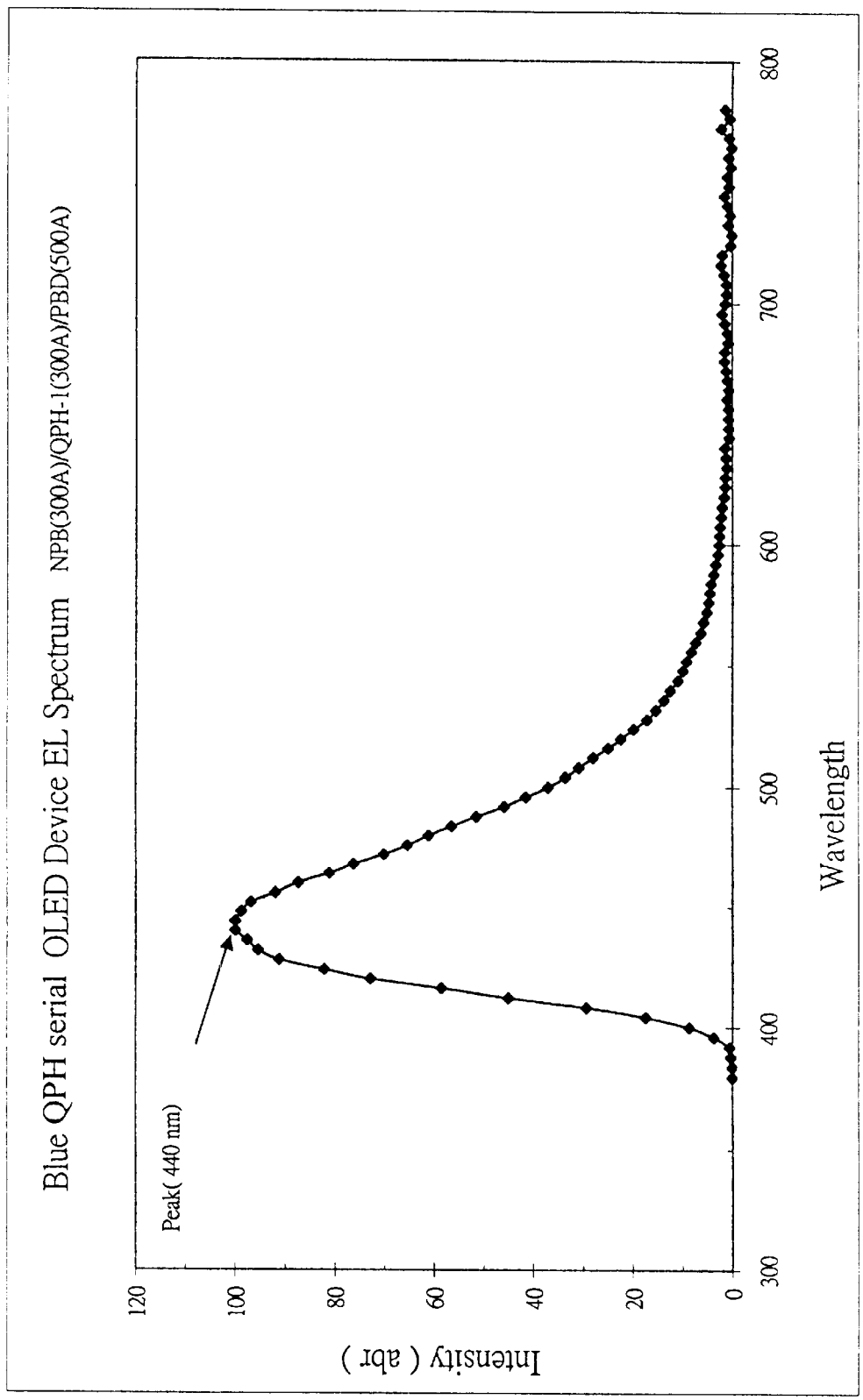
FIG. 4 is a light spectrum from a three-layered organic electroluminescent device incorporating the tertiary amine imparted quaterphenyl compound of the present invention.

FIG. 1 shows that the organic electroluminescent compound of the present invention can also be use in a conventional three-layered organic electroluminescent device. On a clean ITO glass 15, which was formed on a substrate 16, N,N'-bis-(1-naphthyl)-N,N'-diphenyl-1,1'-biphenyl-4,4'-diamine (NPB) was deposited under vacuum ($5\times10^{-6}$ Torr) to a depth of 500 Å to form a hole-transporting layer 14. A tertiary amine imparted quaterphenyl compound (QPH) prepared from one of the above examples was deposited under vacuum to a depth of 300 Å to form a light emitting layer 13. Then biphenyl-p-(t-butyl)phenyl-1,3,4-oxadiazole (PBD)

was deposited on the QPH layer to a depth of 500 Å to serve as an electron-transporting layer 12. Finally a Mg:Ag=10:1 alloy was deposited to serve as a cathode 11. The ITO glass also served as an anode 15. This completed the construction of the three-layered organic electroluminescent device. An electric current of 20 mA was applied to emit a blue color light. The light spectrum is shown in FIG. 4.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A tertiary amine imparted quaterphenyl compound represented by the following formula:

(Formula I)

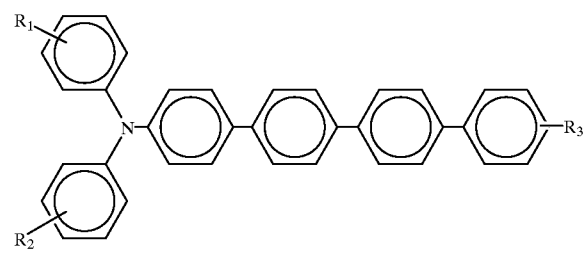

where $R_1$ and $R_2$, which can be different or the same, are hydrogen, $C_1$–$C_5$ alkyl, or $C_6$–$C_{12}$ aryl, and $R_3$ is hydrogen, $C_1$–$C_5$ alkyl, a vinyl group, or an aryl vinyl group.

2. The tertiary amine imparted quaterphenyl compound according to claim 1 which is N-(4'-(1,1-diphenylvinyl) quaterphenyl-4-yl)-N-phenyl-N-(m-tolyl)amine.

3. The tertiary amine imparted quaterphenyl compound according to claim 1 which is N-quaterphenyl-4-yl-N,N-diphenylamine, N-quaterphenyl-4-yl-N-phenyl-N-(m-tolyl) amine, or N-(4'-(1,1-diphenylvinyl)quaterphenyl-4-yl)-N-phenyl-N-(m-tolyl)amine.

4. The tertiary amine imparted quaterphenyl compound according to claim 1 which is synthesized according to the following reaction:

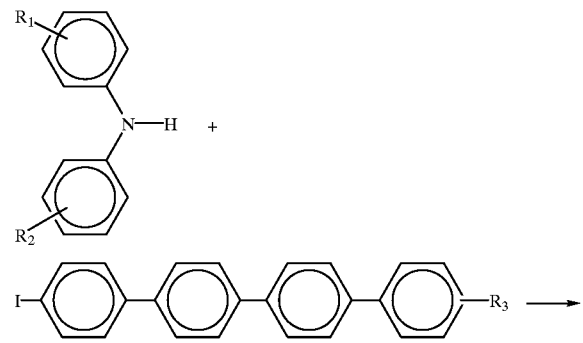

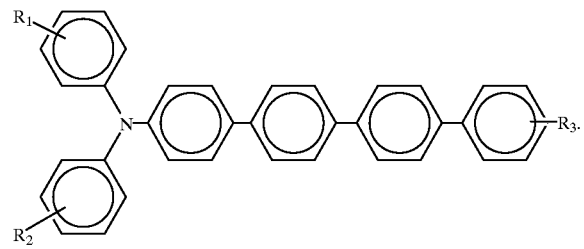

5. The tertiary amine imparted quaterphenyl compound according to claim 1 which is synthesized according to the following reaction:

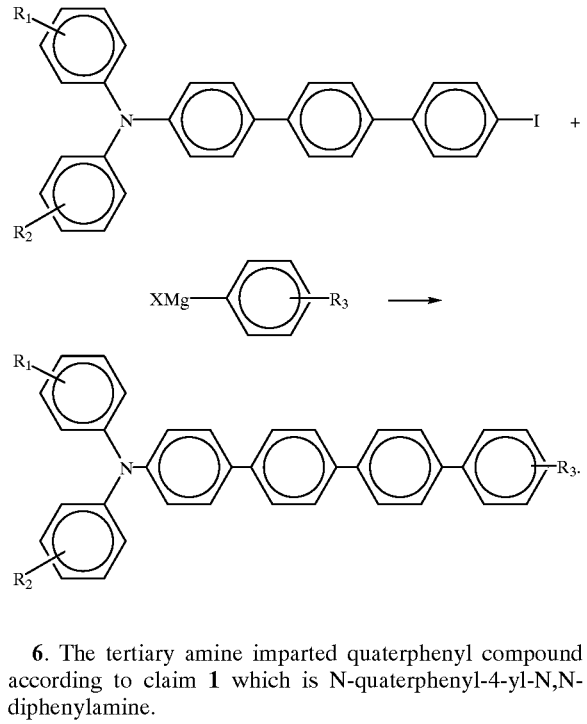

6. The tertiary amine imparted quaterphenyl compound according to claim 1 which is N-quaterphenyl-4-yl-N,N-diphenylamine.

7. A blue color organic electroluminescent device comprising an electron-transporting layer and a hole-transporting layer, wherein said hole-transporting layer also provides light emitting function to serve dual functions as a combined hole-transporting and light-emitting layer;

further wherein said combined hole-transporting and light-emitting layer contains a tertiary amine imparted quaterphenyl compound represented by the following formula:

(Formula I)

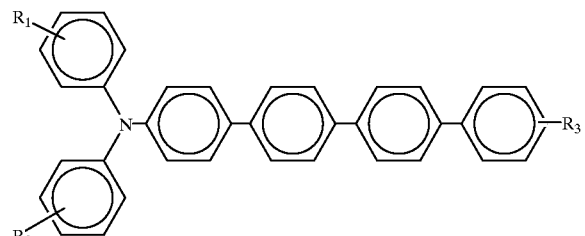

where $R_1$ and $R_2$, which can be different or the same, are hydrogen, $C_1$–$C_5$ alkyl, or $C_6$–$C_{12}$ aryl, and $R_3$ is hydrogen, $C_1$–$C_5$ alkyl, a vinyl group, or an aryl vinyl group.

8. The blue color organic electroluminescent device according to claim 7 wherein said tertiary amine imparted quaterphenyl compound is N-quaterphenyl-4-yl-N,N-diphenylamine, N-(4'-(1,1-diphenylvinyl)quaterphenyl-4-yl)-N-phenyl-N-(m-tolyl)amine, or N-quaterphenyl-4-yl-N-phenyl-N-(m-tolyl)amine.

9. The blue color organic electroluminescent device according to claim 7 wherein said electron-transport layer comprises a metal chelate, 1,3,4-oxadiazole or 1,2,4-triazole or a derivative thereof, a thiopyran sulfone or a derivative thereof, or bis(benzimidazolyl)perylenedicarboximide.

10. The blue color organic electroluminescent device according to claim 9 wherein said metal chelate is aluminum tris(8hydroxyquinoline) or bis (10-hydroxybenzo[h]-quinolinato)beryllium.

11. A blue color organic electroluminescent device comprising an electron-transporting layer, a light emitting layer, and a hole-transporting layer, wherein at least one of said hole-transporting layer and said light emitting layer comprises a tertiary amine imparted quaterphenyl compound represented by the following formula:

(Formula I)

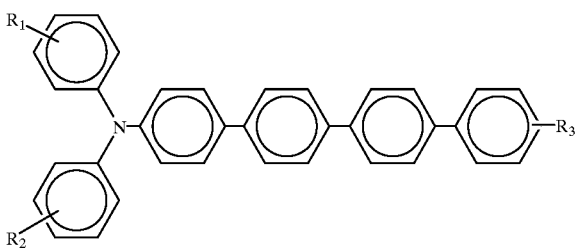

where $R_1$ and $R_2$, which can be different or the same, are hydrogen, $C_1$–$C_5$ alkyl, or $C_6$–$C_{12}$ aryl, and $R_3$ is hydrogen, $C_1$–$C_5$ alkyl, a vinyl group, or an aryl vinyl group.

12. The blue color organic electroluminescent device according to claim 11 wherein said tertiary amine imparted quaterphenyl compound is N-quaterphenyl-4-yl-N,N-diphenylamine, N-(4'-(1,1-diphenylvinyl)quaterphenyl-4-yl)-N-phenyl-N-(m-tolyl)amine, or N-quaterphenyl-4-yl-N-phenyl-N-(m-tolyl)amine.

13. The blue color organic electroluminescent device according to claim 11 wherein said electron-transport layer comprises a metal chelate, 1,3,4-oxadiazole or 1,2,4-triazole or a derivative thereof, a thiopyran sulfone or a derivative thereof, or bis(benzimidazolyl)perylenedicarboximide.

14. The blue color organic electroluminescent device according to claim 13 wherein said metal chelate is aluminum tris(8-hydroxyquinoline) or bis(10-hydroxybenzo[h]quinolinato)beryllium.

15. The blue color organic electroluminescent device according to claim 11 wherein said tertiary amine imparted quaterphenyl compound is N-quaterphenyl-4-yl-N,N-diphenylamine.

16. A process for imparting hole-transportability to a blue light emitting organic electroluminescent compound so that said blue light emitting organic electroluminescent compound can be used in a hole-transporting layer, a blue light emitting layer, or a combined hole-transporting and blue light emitting layer of a multi-layered organic electroluminescent device, said process comprising the step of incorporating a tertiary amino group into said blue light emitting organic electroluminescent compound;

wherein said blue light emitting organic electroluminescent compound with hole-transportability is represented by the following formula:

(Formula I)

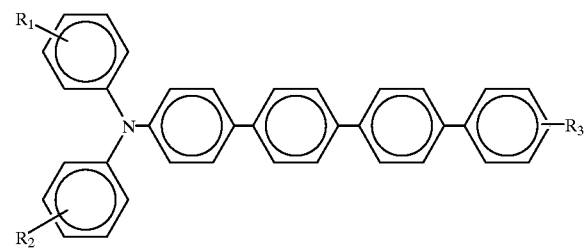

where $R_1$ and $R_2$, which can be different or the same, are hydrogen, $C_1$–$C_5$ alkyl, or $C_6$–$C_{12}$ aryl, and $R_3$ is hydrogen, $C_1$–$C_5$ alkyl, a vinyl group, or an aryl vinyl group.

17. The process for imparting hole-transportability to a blue light emitting organic electroluminescent compound according to claim 16, wherein said blue organic electroluminescent compound with hole-transportability is N-quaterphenyl-4-yl-N,N-diphenylamine, N-(4'-(1,1-diphenylvinyl)quaterphenyl-4-yl)-N-phenyl-N-(m-tolyl)amine, or N-quaterphenyl-4-yl-N-phenyl-N-(m-tolyl)amine.

18. The process for imparting hole-transportability to a blue light emitting organic electroluminescent compound according to claim 16 which is represented by the following reaction:

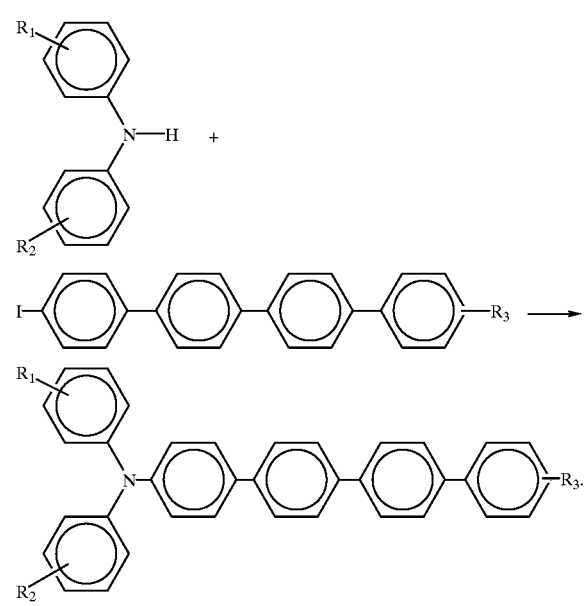

19. The process for imparting hole-transportability to a blue light emitting organic electroluminescent compound according to claim 16 which is represented by the following reaction:

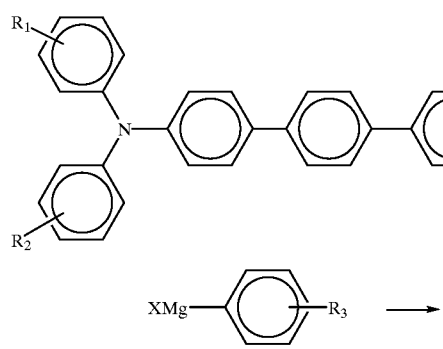

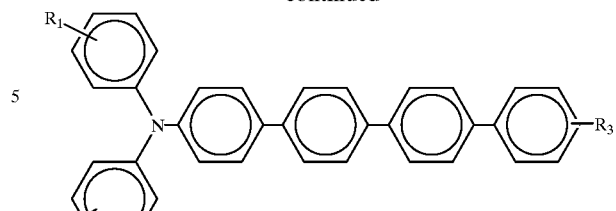

where X is Cl, Br, or I.

20. The process for imparting hole-transportability to a blue light emitting organic electroluminescent compound according to claim 16, wherein said blue organic electroluminescent compound with hole-transportability is N-quaterphenyl-4-yl-N,N-diphenylamine.

* * * * *